United States Patent [19]

Ponsar

[11] 4,000,657
[45] Jan. 4, 1977

[54] APPARATUS FOR MEASURING THE APPARENT WEIGHT OF A SLUDGE CHARGING A LIQUID

[76] Inventor: Yves Marie Ponsar, 6 avenue Marcelin Berthelot, 93250 Villemonble, France

[22] Filed: Sept. 2, 1975

[21] Appl. No.: 609,820

[30] Foreign Application Priority Data

Sept. 9, 1974   France ............................ 74.30429

[52] U.S. Cl. ................................. 73/448; 23/292; 73/444; 73/450
[51] Int. Cl.² ....................... B01L 3/00; G01N 9/12
[58] Field of Search .......... 73/32 R, 444, 445, 446, 73/448, 450; 210/85, 86; 23/230 R, 230 B, 292; 195/103.5 R

[56] References Cited

UNITED STATES PATENTS

| | | | |
|---|---|---|---|
| 1,972,220 | 9/1934 | Edelmann | 73/448 |
| 2,132,015 | 10/1938 | Collins | 73/450 |
| 2,221,913 | 11/1940 | Edelmann | 73/448 |
| 2,506,973 | 5/1950 | Segal | 73/450 |
| 2,625,641 | 1/1953 | Jenkins | 73/444 X |
| 3,827,306 | 8/1974 | Youngs | 73/450 |

*Primary Examiner*—Morris O. Wolk
*Assistant Examiner*—Michael S. Marcus
*Attorney, Agent, or Firm*—Young & Thompson

[57] ABSTRACT

Apparatus for measuring and monitoring the state of activated sludge in the continuous treatment of waste waters or sewage. A suspensoid is produced by clarifying a quantity of the sludge-charged liquid, and the apparent weight of the sludge relative to the suspensoid is derived and is used as an indication of the state of the treatment installation. The apparatus is easily transportable and can be used on site.

8 Claims, 7 Drawing Figures

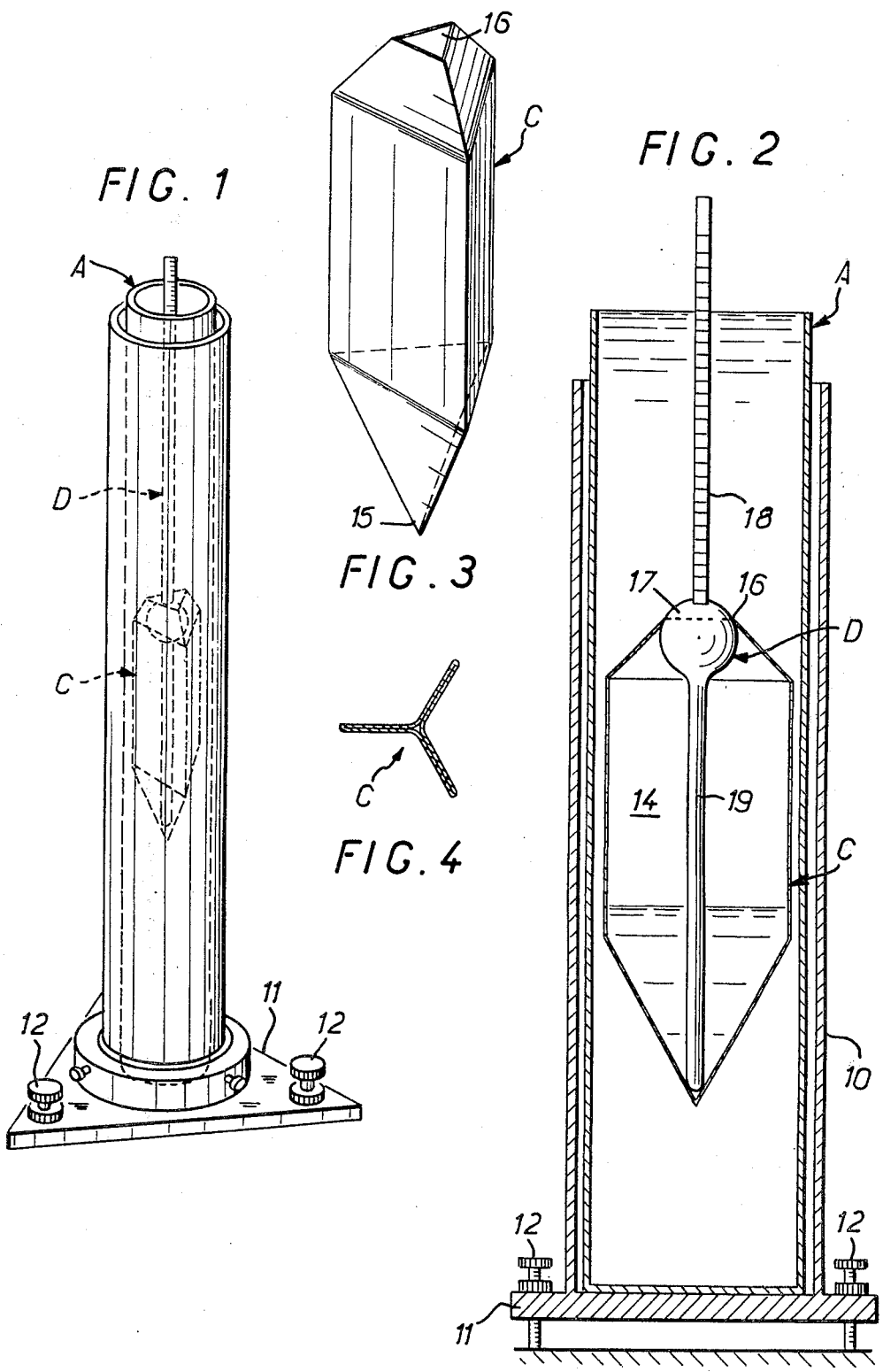

APPARATUS FOR MEASURING THE APPARENT WEIGHT OF A SLUDGE CHARGING A LIQUID

BACKGROUND OF THE INVENTION

1. Field of the Invention

This invention relates to apparatus for measuring the initial apparent weight and subsequent changes of a sludge charging a liquid.

In numerous cases of treatment of liquids, particularly of waste water or sewage, it is often necessary to utilise live sludge the evolution of which must be monitored not only from day to day at a given point in the treatment installation, but also at a given moment from one point to another in the installation.

2. Description of the Prior Art

In treatment stations which employ activated sludges, the volume occupied by this sludge after settling for half an hour in a test-tube is measured first in the proximity of treatment basins, and secondly the weight of the dry extract is measured in the laboratory.

After these successive measurements, and with these two concentrations expressed as volume and as weight respectively, the first measurement in millilitres per litre is divided by the second in grams per litre to define a specific volume, which is called the sludge index, quality index, or Mohlman index.

Any inaccuracy or difficulty in either of the terms of the division is reflected in the index.

A first difficulty consists in determining the compacted volume read after settling for half an hour. For a sludge of a given nature this volume is no longer proportional to the weight of the dry extract when the volume or weight concentration exceeds a relatively low limit.

It has already been proposed to predilute the sample of sludge which is to be analysed in such a manner that, after settling for 30 minutes in a 1-litre test tube the compacted volume will be between 150 and 250 millilitres. This presupposes at least one additional preliminary test and there is a consequent waste of time.

A second difficulty arises from the lengthy preparation of the dry extract by centrifuging and stoving before weighing, preceded by any transporting necessary before reaching a laboratory. Knowledge of the weight is generally at best acquired only on the day following the taking of the sample. Moreover, the division operation giving the specific volume is often put off until the next day, and even later in the case of small stations which have no laboratory. Any action required to regulate the installation once the full facts are known is therefore correspondingly delayed.

Moreover, in the case of an increase of the pollution to be treated, the living matter (biomass) of the sludge, which necessarily increases, also causes an increase of the weight of the dry material. Excess sludge has to be drained in an undesirable manner.

Apart from delays of this kind, weighing in the dry state gives rise to other difficulties. It requires nontransportable equipment which is expensive to purchase and to install, because a local laboratory is required, and is expensive to operate because a specialist is needed. In cases where the laboratory is not on the spot it is difficult to coordinate the data from the laboratory, which has knowledge only of the sludge, and data from the treatment station where the circumstances inside and outside the station are known.

Moreover, the sludge reduced to its dry extract does not provide information regarding its weight in the water and its ability to settle, and still less regarding the evolution of this weight of a material, which in reality is a live material, both in the water and in the successive states of oxygenation followed by a lack of oxygen.

In order to facilitate the operation of one or more treatment stations, it is a main object of the present invention to eliminate the difficulties and delays mentioned above, to account for variations in life, temperature, and in the ambient condition, to note the effects thereof; to combine all the measurements in a single place, the treatment station, using the same personnel, and to provide an economical, transportable apparatus which is easy to use even out-of-doors.

A further object of the invention is to enable the operator to intervene in practice at his station within the shortest possible time, such time being further shortened by the fact that in the event of an increase of pollution which is to be treated, the naturally increasing biomass does not necessarily increase the apparent weight and may even reduce it. This avoids undesirable draining operations referred to previously.

The present invention provides apparatus for measuring the apparent weight of sludge charging a liquid, comprising a thermally insulating container, a buoyant vessel shaped to fit into the thermally insulated container for immersion in liquid in the container, and a supporting and reference level probe for the buoyant vessel comprising a ball adapted to engage in an opening in the buoyant vessel and a graduated rod surmounting the ball.

BRIEF DESCRIPTION OF THE DRAWINGS

Embodiments of the invention are described below, by way of example, with reference to the accompanying drawings, in which:

FIG. 1 is a general view in perspective of apparatus according to the invention including a container and a bag provided with a probe;

FIG. 2 is a similar view to FIG. 1, but in vertical section;

FIG. 3 is a view in perspective of the bag with the shape which it assumes when it is full;

FIG. 4 is a view in cross-section of the bag with the shape which it assumes when it is empty;

DESCRIPTION OF THE PREFERRED EMBODIMENTS

Figure 5:
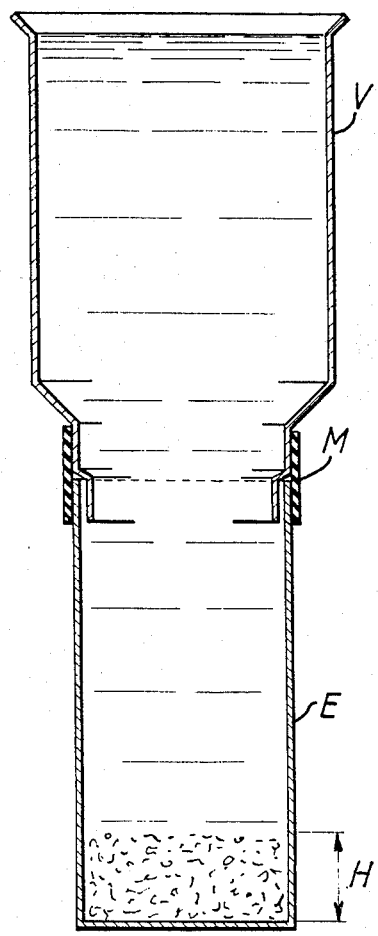
FIG. 5 shows a test-tube with a dilution vessel for measuring a positive index for a sludge denser than a suspensoid.

The embodiment illustrated in FIGS. 1 to 5 relates to monitoring a sludge which is denser than the suspensoid, particularly an activated sludge in an installation for treating waste water or sewage for example.

The suspensoid is the sludge-charged liquid after clarification.

The invention provides a device for measuring the quality of the sludge in terms of its specific volume, in order to check the operation of the installation, and provide information which enables adjustment of the installation to restore correct operation, to be carried out without undue delay.

The device is illustrated in FIGS. 1 to 4 and comprises a container A in a thermal protection device, a buoyant vessel in the form of a bag C, and a probe D. A wind shield may also be provided.

In greater detail, the device comprises as shown in FIGS. 1 and 2, a thermal insulation tube 10 mounted on a base 11, which is maintained horizontal by means of adjustable screws 12. The container A is of cylindrical shape and is transparent, and is removably housed in the tube 10.

The bag C, FIG. 2, forms a vessel 14 which is adapted to be immersed in the container A. The bag C is made of polyamide film or other plastics material having a low coefficient of water absorption and having appreciable wettability. The bag C is of prismatic shape and, when empty, collapses to a star-shaped cross-section as shown in FIG. 4 and can be folded flat for transport, and is prismatic when it is full, for instance with a triangular cross section as shown in FIG. 3.

The bag C has a pointed bottom end 15 and at its top end has a narrow opening 16 of triangular shape as illustrated in FIG. 3.

The probe D fits into the bag C with the hollow glass ball 17 engaging in the opening 16, and thereby acts as a floatation support for the bag C and a level indicating means.

The probe D comprises a hollow glass ball 17 surmounted by a graduated rod 18 and is extended downwardly as tail 19 which acts as stabilisation ballast.

The respective coefficients of expansion of the polyamide of which the bag C is made, and of the glass of which the ball 17,, and optionally the tail 19, are made, are such that measurements are not falsified if a temperature change occurs.

A test-tube E, FIG. 5, is shaped to receive a dilution vessel V which is relatively large and the volume of which is at least one and a half times that of the test tube E. The volume of the test tube E is for example 1 liter and that of the vessel V 1.5 liter. A rubber sleeve M around the junction of the vessel V and the test tube E provides a seal.

For the purpose of measuring the quantity of sludge charging the liquid in a waste water treatment unit there are used on the one hand an amount of charged liquid and on the other hand an amount of suspensoid corresponding to said charged liquid.

Some of the suspensoid is poured into the container A, at least as far as an upper mark. The bag C is immersed in this container A and is filled with the suspensoid by means of a funnel until it overflows.

The position of the reference mark is such that the container A is then full. The bag C is checked to ensure that it is actually full and that no air bubbles cling to its wall. The probe D is introduced into the bag C in such a way that the float ball 17 is engaged in the opening 16 so that the probe D is fastened to the bag C.

The position of equilibrium of the bag, that is the calibration, is noted by observing the position of the rod 18 relative to the level of liquid in the container A. This is preferably done by sighting below the surface level of the suspensoid.

The suspensoid is replaced in the bag C by charged liquid, and the new position of equilibrium of the bag C is noted by observing the position of the bar 18 relative to the level of liquid in the container A.

The difference in level of immersion of the bag C and the probe D for the two measurements gives the apparent weight of the sludge. The scale on the probe D is normally such as to give a direct reading of the difference in grams per liter of sludge relative to the suspensoid. The inverse of this reading gives in liters the volume of liquid corresponding to one gram of sludge.

The test tube E and the dilution vessel V are filled with suspensoid, and a volume of charged liquid corresponding to one gram of sludge is added.

For example, if the first two-stage measurement in the apparatus of FIG. 2 shows that the sludge has a weight of 1.25 kilograms per liter; 1/1.25 = 0.8 liter of charged liquid is added to the liquid in the vessel V.

The sludge is allowed to settle to the bottom of the test tube E, as shown in FIG. 5, for a predetermined time, for example half an hour, and the height H of compacted sludge in the bottom of the test tube E is measured, thereby ascertaining the compaction volume per unit of weight of sludge, for example 400 milliliters per kilogram.

In order to ascertain the volume of the deposit corresponding to one liter of sludge in its natural state, it is sufficient to multiply 1.25 kilograms per liter by 400 milliliters per kilogram, to obtain 500 milliliters per liter, that is to say 50%.

The operations just described, which are based originally on measurement of the sludge in its natural state, are very quick and take little more than half an hour. Practical interventions to modify the operation of the installation can be effected immediately afterwards. Up to the present time this has been inconceivable.

Emptying of excess activated sludge can even be effected as soon as the weighing has been made, so as to operate with a suitable apparent weight, because the initial variations of this weight are the inverse of the variations of pollution loading.

These inexpensive operations may be repeated without difficulty, either as confirmation, or, half a day later, to measure the effects achieved by the intervention to regulate operation of the installation.

The process and device are particularly advantageous because of the economy of means used, the fact that no special premises are required, and that the apparatus can be entrusted to the operator of the installation himself, in which case all the information is concentrated on site and is available to the same person.

The same person may return one hour or two hours later to measure, from the reduction of the apparent weight, the volume of any gas produced and retained in the sludge in the bag C in the form of extremely fine bubbles which are often of nitrogen, thereby determining any change in the apparent weight of the sludge due to denitrification. This gives information regarding troublesome phenomena which can occur at certain points in the installation, in particular the bottom of the clarifier. By agitating the deposit of sludge in the bag, the initial weight can be obtained again and verified.

Predilution of the sludge in the test tube can be effected in an accurate manner and without any preliminary settling test.

The apparatus is very easily transportable, particularly as its components can be stored inside each other, so that a single apparatus in the hands of a single technical operator can easily serve at least two stations a day, where it is desired to known the nature of the sludge, notably its apparent weight and volume, its quality in terms of specific volume, and its possible aptitude to form gas in particular by denitrification.

The apparatus has numerous other applications for example for weighing a suspensoid charged with salts by comparison with pure water. Such a suspensoid is often found in aerobic digested sludges.

Temperature equilibrium is maintained with the aid of the thermal protection jacket 10. Another application is for weighing the sludge used for treating drinking water.

The invention is not limited to the examples just described but also embraces variations thereof. It is also applicable to measurements of sludges which are lighter than the suspensoid or other products.

Figure 7:
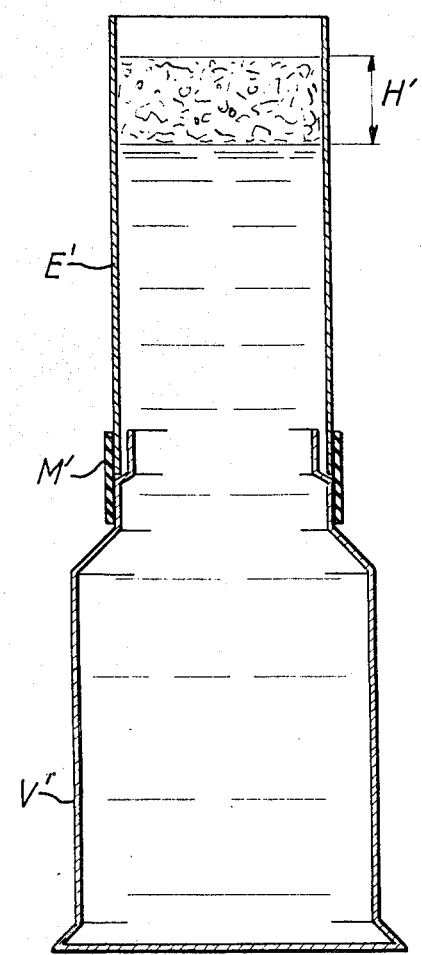
FIG. 7 is a view similar to FIG. 5, but relates to a modified test-tube with a dilution vessel for measuring a negative index of a sludge less dense than the suspensoid.
Figure 6:
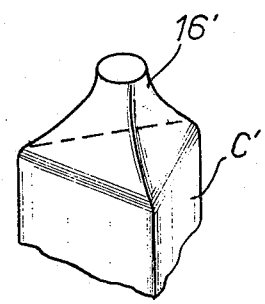
FIG. 6 is a partial view similar to FIG. 3, but relating to a modified form of the opening of the bag, which is usable particularly with a sludge less dense than the suspensoid.

FIGS. 6 and 7, show apparatus for use when the sludge is less dense than the suspensoid.

In FIG. 6 the bag C has a top opening 16' with a slightly elongated, narrowed neck to permit fluid-tight engagement with the ball 17 on the probe and thereby prevent the sludge from escaping from the bag C' during the operation for determining the apparent weight of the sludge.

The container A and the probe B are the same as those described with reference to FIGS. 1 to 4. However, an additional weight is placed on the movable parts before calibration.

The test tube designated E', FIG. 7, has an end which engages with a dilution vessel V', but the test tube E' has no bottom and is fitted to the top of the vessel V'. The joint is sealed by a sealing sleeve M'.

When the apparent weight of the sludge has been determined in the manner described with reference to FIGS. 1 to 4, this apparent weight being negative, an amount of charged liquid corresponding to one unit of weight of the sludge is poured into the vessel V', and then the vessel V' and test tube E' are filled as far as a top graduation on the test tube E'.

The sludge is allowed to rise to the top for a predetermined time, for example half an hour, and the height H' of sludge accumulated at the top of the test tube is measured, this giving the compaction volume per unit of weight of sludge and consequently the quality index of the sludge.

It will be appreciated that the quantity and quality are here preceded by the minus sign, which distinction is not possible in measurements utilising a dry extract.

I claim:

1. Apparatus for measuring the apparent weight of sludge charging a liquid, comprising a thermally insulated container having an open end, a bag shaped to fit into the said container for immersion in liquid in the said container, said bag being starshaped when empty and collapsed and expanding to a triangular cross-section when full, said bag having an upper opening, a buoyant ball engaged within said bag beneath said opening thereof for supporting said bag, and a graduated rod surmounting the ball for measuring the level of the bag and ball assembly.

2. Apparatus as claimed in claim 1 further having a tail secured to the lower side of the ball which extends down adjacent to the bottom of the bag and acts as a stabilization ballast.

3. Apparatus for measuring the apparent weight of sludge charging a liquid, comprising a thermally insulated container having an open end, a bag shaped to fit into the said container for immersion in liquid in the said container, said bag being a bag of polyamide film which collapses to a star-shape when empty and expands to a triangular cross-section when full, said bag having an upper opening, a buoyant ball engaged within said bag beneath said opening thereof for supporting said bag, and a graduated rod surmounting the ball for measuring the level of the bag and ball assembly.

4. Apparatus as claimed in claim 1 further having a tail secured to the lower side of the ball which extends down adjacent to the bottom of the bag and acts as a stabilization ballast.

5. Apparatus for measuring the apparent weight of sludge charging a liquid, comprising a thermally insulated container having an open end, a collapsible bag shaped to fit into the said container for immersion in liquid in the said container, said bag having an upper opening, a buoyant ball engaged within said bag beneath said opening thereof for supporting said bag and a graduated rod surmounting the ball for measuring the level of the bag and ball assembly.

6. Apparatus as defined in claim 5 wherein said bag is star-shaped when empty and collapsed and expands to a prismatic shape when full.

7. Apparatus as defined in claim 5 wherein said bag is made of polyamide.

8. Apparatus as defined in claim 5 further having a tail secured to the lower side of the ball which extends down adjacent to the bottom of the bag and acts as a stabilization ballast.

* * * * *